(12) United States Patent
Shalaby

(10) Patent No.: US 7,709,556 B2
(45) Date of Patent: *May 4, 2010

(54) RADIATION AND RADIOCHEMICALLY STERILIZED ABSORBABLE DEVICES WITH DOSE-CONTROLLED FUNCTIONAL STRENGTH RETENTION

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1029 days.

This patent is subject to a terminal disclaimer.

(21) Appl. No.: 10/683,060

(22) Filed: Oct. 9, 2003

(65) Prior Publication Data

US 2004/0133237 A1 Jul. 8, 2004

Related U.S. Application Data

(60) Provisional application No. 60/417,253, filed on Oct. 9, 2002.

(51) Int. Cl.
 C08J 3/28 (2006.01)
 C08F 2/48 (2006.01)
 C08F 2/42 (2006.01)
 A61K 47/00 (2006.01)

(52) U.S. Cl. .............. 523/111; 523/105; 523/112; 523/113; 522/150; 522/152; 522/153; 522/173; 522/182; 422/1; 422/22; 422/23; 422/25; 424/444; 602/48; 602/49; 514/772.3

(58) Field of Classification Search ............ 422/22, 422/23, 25, 1; 424/444; 602/48, 49; 514/772.3; 522/150, 152, 153, 173, 182; 523/111, 105, 523/112, 113
See application file for complete search history.

(56) References Cited

U.S. PATENT DOCUMENTS

| | | | |
|---|---|---|---|
| 4,429,080 A | 1/1984 | Casey et al. | |
| 4,435,161 A | 3/1984 | Mosimann | |
| 4,532,928 A | 8/1985 | Bezwada et al. | |
| 4,649,921 A | 3/1987 | Koelmel et al. | |
| 5,133,739 A | 7/1992 | Bezwada et al. | |
| 5,350,798 A | 9/1994 | Linden et al. | |
| 5,422,068 A | 6/1995 | Shalaby et al. | |
| 5,485,496 A * | 1/1996 | Lee et al. | 378/64 |
| 5,530,037 A * | 6/1996 | McDonnell et al. | 522/79 |
| 6,255,408 B1 | 7/2001 | Shalaby | |
| 6,299,631 B1 | 10/2001 | Shalaby | |
| 6,342,065 B1 | 1/2002 | Shalaby | |
| 6,462,169 B1 | 10/2002 | Shalaby | |
| 6,498,229 B1 | 12/2002 | Shalaby | |
| 6,503,991 B2 | 1/2003 | Shalaby | |
| 6,579,916 B1 * | 6/2003 | Askill et al. | 522/152 |
| 6,897,245 B2 * | 5/2005 | Gen | 514/772.3 |
| 7,351,426 B2 * | 4/2008 | Shalaby et al. | 424/448 |
| 2002/0028231 A1 * | 3/2002 | Hierlemann et al. | 424/444 |
| 2004/0199207 A1 * | 10/2004 | Shalaby et al. | 606/214 |

* cited by examiner

*Primary Examiner*—Sanza L McClendon
(74) *Attorney, Agent, or Firm*—Leigh P Gregory

(57) ABSTRACT

Absorbable radiation or radiochemically sterilized medical devices, including sutures, whose breaking strength and absorption profile can be modulated by controlling the total dose received during sterilization are disclosed.

7 Claims, No Drawings

RADIATION AND RADIOCHEMICALLY STERILIZED ABSORBABLE DEVICES WITH DOSE-CONTROLLED FUNCTIONAL STRENGTH RETENTION

This application claims the benefit of prior provisional application U.S. Ser. No. 60/417,253, which was filed on Oct. 9, 2002.

FIELD OF THE INVENTION

The invention relates to modulating the in-use profile of mechanical property retention of absorbable medical devices by controlling the total dose they receive during sterilization by high energy radiation, thus broadening the scope of their clinical applications.

BACKGROUND OF THE INVENTION

When exposed to a sterilizing dose of high-energy radiation, absorbable polymers, particularly fully aliphatic ones, are known to undergo catastrophic reduction in their functional strength retention when used as implants for wound repair [Chapter 1 in *Biomedical Polymers—Designed-to-Degrade Systems* (Shalaby, Ed) Hanser, N.Y., 1994]. Because of the detrimental effects of high-energy radiation, such as gamma radiation and electron-beam, on absorbable polymers and their intermediates, two novel approaches were disclosed in the prior art to allow the application of high-energy radiation in the sterilization of absorbable devices. The first approach dealt with incorporating a significant fraction of aromatic repeat units in the chain of absorbable aliphatic polyesters [U.S. Pat. Nos. 4,435,161 (1984), 4,532,928 (1985), and 4,649,921 (1987)]. Although this was an effective means for allowing copolymers of glycolide with aromatic prepolymers to be radiation sterilizable, the approach has limited applicability to other absorbable copolymers and its implementation is technically tedious and costly. The second approach dealt with using a combination of a very low dose of high-energy radiation and radiolytically generated formaldehyde as a gaseous co-sterilant and resulted in a minimum or no detrimental effects on the sterilized absorbable polymers [U.S. Pat. No. 5,422,068 (1995)]. This was referred to as radiochemical sterilization. Meanwhile, there has been a growing need for absorbable polymers and intermediates having a broad range of strength retention profiles for use in many surgical and tissue repair procedures. Another area with pressing need for absorbable polymers with a broad range of functional strength retention profiles pertains to their use in tissue engineering as scaffolds for supporting the propagation of several types of viable cells for different periods of time, as in the case of endothelial cells and osteoblasts. To meet the needs for these wide-ranging applications will require decades of research to develop and test the biocompatibility of many candidate absorbable polymers and intermediates without limited assurance for success. Accordingly, the present invention deals with the use of a unique family of fully aliphatic, absorbable polymers as the source of several subfamilies of polymers through controlling the total dose of high-energy radiation received by the specific substrate to achieve sterility. Such a unique family of polymers is distinguished for having segmented or blocked copolymeric chains with radio-compatible components (i.e., components capable of limiting the radiolytic impact of high-energy radiation), wherein said polymers can display a range of functional strength retention profiles through modulating the radiation dose, and sterility can be secured through a radiolytically generated surface sterilant at radiation doses of less than 25 kGy. Likewise, intermediates for flexible absorbable articles, which are present as liquids at room temperature, can be considered as candidates for being radio-compatible systems.

SUMMARY OF THE INVENTION

The present invention deals with absorbable biomedical devices, such as surgical sutures, made of segmented/block copolymers and having a broad range of clinically useful functional properties which can be modulated in degrading environments through controlling their exposure to high energy radiation and, hence, the total dose they receive during radiochemical or radiation sterilization using gamma rays or electron beam.

Thus, the present invention is directed to a method for sterilizing and modulating the physical properties of absorbable, ester-based medical devices which includes the steps of providing a medical device formed of an absorbable, ester-based polymer, and irradiating the medical device with high energy radiation at a dose in the range of from about 3 kGy to about 50 kGy; wherein the physical properties vary inversely with the radiation dose. In one embodiment the absorbable ester-based polymer is the polymerization product of methoxyalkyl cyanoacrylate and the device is a tissue adhesive, and the controlled physical properties include adhesive joint strength when the tissue adhesive is applied to living tissues. Alternatively for such a tissue adhesive the polymerization product of methoxyalkyl cyanoacrylate may be modified by a further compliant absorbable copolyester. When the radiation dose is less than 25 kGy the tissue adhesive can be stored in a sealed plastic ampoule within a secondary package containing a polymer capable of radiolytically generating gaseous formaldehyde to complement the radiation dose as costerilants. Regardless of the type of medical device formed, the high energy radiation may be gamma-rays or electron beam.

In another aspect the present invention is directed to a sterilized, absorbable ester-based medical device having controlled physical properties made by a process which includes the steps of providing an absorbable, ester-based polymer which is a high glycolide-based polymer, forming the polymer into a desired medical device configuration, and irradiating the formed device with high energy radiation at a dose in the range of from about 3 to less than 25 kGy, wherein the radiation is complemented by a radiolytically generated formaldehyde as a costerilant. In one embodiment the device is a surgical suture and the controlled physical properties include controlled mass loss and breaking strength profiles in the biologic environment. A preferred high-glycolide polymer is a segmented or block copolymer which has at least 50 percent by weight of glycolide-based sequences, the copolymer having a hard segment or block which is greater than about 80 percent by weight glycolide and less than about 20 percent by weight of a monomer such as l-lactide or trimethylene carbonate, and a soft segment or block derived from at least one cyclic monomer such as caprolactone, trimethylene carbonate, lactide, p-dioxanone, or 1,5-dioxepan-2-one. Preferably the polymer is a segmented or block copolymer having a polyaxial chain geometry wherein the soft segments or blocks are an amorphous core and wherein the hard segments or blocks are crystalline terminal segments or blocks. For this type of polymer a preferred medical device is a surgical suture and the controlled physical properties include the mass loss and breaking strength retention profiles of the suture in the biologic environment.

In yet another aspect the present invention is directed to a sterilized, absorbable ester-based medical device having controlled physical properties made by a process which includes the steps of providing an absorbable, ester-based polymer comprising a high lactide-based polymer, forming the polymer into a desired medical device configuration, and irradiating the formed device with high energy radiation at a dose in the range of from about 3 to less than 25 kGy, wherein the radiation is complemented by a radiolytically generated formaldehyde as a costerilant. A preferred high lactide-based polymer is a segmented or block copolymer having at least 60 percent by weight of l-lactide-based sequences, the copolymer having a hard segment or block which is greater than about 85 percent by weight l-lactide and less than about 15 percent by weight of a monomer such as trimethylene carbonate, caprolactone, or glycolide, and a soft segment or block derived from at least one cyclic monomer such as caprolactone, trimethylene carbonate, lactide, p-dioxanone, or 1,5-dioxepan-2-one.

Alternatively, the present invention is directed to a sterilized, absorbable ester-based medical device having controlled physical properties made by a process which includes the steps of providing an absorbable, ester-based polymer comprising a high lactide-based polymer, forming the polymer into a desired medical device configuration and irradiating the formed device with high energy radiation at a dosage in the range of from 25 kGy to about 50 kGy. A high lactide polymer as described above is also suitable for use in forming this medical device.

DETAILED DESCRIPTION OF THE PREFERRED EMBODIMENTS

This invention deals, in general, with radiation or radiochemically absorbable medical devices exhibiting radiation dose-controlled functional strength retention properties upon aging in degrading environments. The radiation and radiochemically sterilized devices, subject of this invention, can be in the form of a suture, woven and knitted mesh or tape, clip, bone screw, bone plate, and any of the absorbable constructs used in general, vascular, plastic, and orthopedic surgeries. A specific aspect of this invention deals with radiation or radiochemically sterilized absorbable sutures made of segmented or block copolymers exhibiting breaking strength retention profiles that can be modulated by controlling the total radiation dose received during sterilization. A specific aspect of this invention deals with a total dose of high-energy radiation ranging between 3 and 50 kGy. At radiation doses of less than 25 kGy, sterility will be achieved by placing the absorbable device in a sealed package containing a small amount of polyformaldehyde capable of radiolytically generating gaseous formaldehyde as described in the prior art on radiochemical sterilization [U.S. Pat. No. 5,422,068 (1995)]. When the absorbable device is polymeric, it is intended to have a segmented or block copolymeric chain where one of the segments (or blocks) constitutes an amorphous, highly flexible component and the second segment (or block) constitutes a hard crystalline component. The soft segment is intended to absorb the high-energy radiation and dissipate the associated energy following the primary radiolytic events and hence, minimize chain degradation known to take place during the secondary events. Accordingly, the overall degradation effect of high-energy radiation will be minimized because of the mediating role of the mobile (having a glass transition temperature of less than about 30° C.) amorphous segment or block. This results not only in minimized degradation, but also produces a more predictable response as compared to cases where the device is made of linear, rigid, less mobile homopolymeric or random copolymeric chains as in polyglycolide or a 90/10 glycolide/lactide random copolymer. Consequently, when an absorbable, segmented or block copolymer is converted to a monofilament suture, braided suture, or other forms of textile constructs, such as a woven or knitted absorbable mesh or non-woven, melt-spun and electrospun microfabrics or other fiber constructs, the radiation dose can be used in concert with a radio-compatible component to control the chain degradation and consequently, modulate the breaking strength retention profile and other relevant properties as the absorbable device, being a suture or mesh, or any allied construct, commences to degrade in the biologic environment. Among these segmented or block copolymers in the form of surgical sutures in which the breaking strength retention profile can be modulated by varying the dose are those noted in the prior art described in the following U.S. Pat. Nos. 4,429,080 (1984), 5,133,739 (1992), 6,255,408 (2001), 6,342,065 (2002), 6,462,169 (2002), 6,498,229 (2002), and 6,503,991 (2003). More specifically, the segmented or block copolymers are made of a soft, amorphous segment or block made of one or more cyclic monomer such as caprolactone, trimethylene carbonate, glycolide, lactide, p-dioxanone, 1,5-dioxapan-2-one while the hard segment or block is crystalline and made of more than 50 percent glycolide or l-lactide. In another specific aspect of this invention, the amorphous segment is present as a core of a polyaxial, segmented copolymer while the hard crystallizable segment constitutes the terminals of the polyaxial molecule as described in U.S. Pat. No. 6,462,169 (2002). Another specific aspect of this invention deals with an absorbable device made of segmented or block copolymer wherein the blocks or segments are part of a linear chain and arranged in an ordered or random manner along the chain axis as described in U.S. Pat. Nos. 6,255,408 (2001), 6,342,065 (2002), 6,498,229 (2002), and 6,503,991 (2003).

Another aspect of this invention deals with use of a dose modulation of high-energy radiation to shorten the time required for absorbable devices and particularly braided sutures to undergo practically complete mass loss or simply the time required for practically complete absorption at the implant site in the biologic environment or simulated in vitro conditions. More specifically, the invention deals with the use of dose modulation of the properties of long-lasting devices, such as high lactide-based (i.e., based on more than 60% of lactide-derived chain sequences) sutures and particularly braided ones. Furthermore, a specific aspect of this invention deals with using radiation dose modulation for shortening the breaking strength retention (BSR) profile of segmented high-lactide braided sutures and the time for practically complete mass loss (i.e., more than 90%). The mass loss can be determined in vivo by monitoring the reduction of the suture cross-sectional area. Alternatively, the mass loss can be determined gravimetrically by incubating the suture in phosphate buffer at pH 7.4 and 37° C. to simulate the in vivo environment. For long-lasting sutures, an accelerated in vitro mass loss protocol can be used for comparative purposes at pH of 12 and 50° C. These conditions can also be used to evaluate and compare the accelerated in vitro mass loss profiles of long-lasting, high-lactide sutures.

Another aspect of this invention deals with a liquid device that undergoes conversion into a solid upon contacting an aqueous biological site. The liquid device is intended to behave similarly to the amorphous segment or block in the segmented copolymer regarding the response to high-energy radiation. Typical examples of the liquid devices are the precursors of absorbable tissue adhesives, which are formulations of an amorphous or liquid absorbable polyester and a methoxyalkyl cyanoacrylate. The absorbable polyester is used primarily as a polymeric modifier to increase the compliance of the cured cyanoacrylate monomer. Other additives or modifiers can be present in the cyanoacrylate formulations as descried in U.S. Pat. Nos. 5,350,798 (1994) and 6,299,631 (2002). In addition to modulating the properties of the cured tissue adhesive formulations through the use of the absorbable polyester as modifier, the properties of the cured adhesives can be uniquely modulated by controlling the dose of the high energy radiation used during radiochemical sterilization. In effect, the radiation dose can affect the radiation-induced polymerization of the cyanoacrylate monomer which, in turn, affects the unreacted monomer content and viscosity of the sterilized formulation, and subsequently, changes the curing process and final properties of the adhesive. In contrast, the high energy radiation can be used to control the molecular weight of the polyester modifier which can have the opposite effect on the formulation. Therefore, one can control the radiation dose to produce an array of sub-formulations having a range of properties that are different from those of the parent formulation. Indirectly, this leads to a family of tissue adhesives that can provide adhesive joints with a range of adhesive joint strength retention profiles when used clinically. A more specific aspect of this invention deals with a tissue adhesive formulation in a sealed primary package in the form of a small plastic ampoule with a tapered neck within a hermetically sealed secondary package containing polyformaldehyde that is capable of radiolytic generation of formaldehyde gas when the entire package is exposed to less than 25 kGy gamma radiation. A more specific aspect of this invention deals with a methoxypropyl cyanoacrylate formulation containing a copolyester modifier in sealed polyethylene ampoules that are, in turn, enclosed in a primary sealed, secondary package containing Celcon-M90 polyformaldehyde powder and irradiated with 4 to 7 kGy of gamma radiation to yield a sterile product.

The present invention can be further illustrated by the following examples:

Radiation and Radiochemically Sterilized Absorbable Suture Braid with Dose-Modulated Breaking Strength Retention (BSR) Profile Three sets of braided sutures were prepared using three types of segmented copolyesters having amorphous soft and crystalline hard segments as described in U.S. Pat. No. 6,342,065 (2002). The compositions of the braids are noted in Table I. The effects of the total gamma radiation dose used for sterilization on the in vitro and in vivo breaking strength retention (BSR) of different sutures are summarized in Tables II to IV. Depending on the total dose, both the traditional 25-27 kGy and radiochemical sterilization processes were used to study the dose-controlled BSR.

TABLE I

Braid Composition Based on Polymerization Charge

| Braid of Ex. No. | Initial Monomer* Fraction | Initial Overall Monomer Composition | | |
|---|---|---|---|---|
| | | L | T | C |
| 1 | 8-92 T - (96/4 L/T) | 88.32 | 11.68 | — |
| 2 | 8-92 T - (93/7 L/T) | 85.6 | 14.4 | — |
| 3 | 10-90 (50/50 C/T) - (93/7 L/T) | 83.7 | 11.3 | 5.0 |

*T = trimethylene carbonate;
L = l-lactide;
C = ε-caprolactone.

TABLE II

Dose-modulated BSR Data for the Braided Suture of Example 1

| | Initial Physical Properties | | | % BSR | | | |
|---|---|---|---|---|---|---|---|
| | | | | In Vitro @ 37° C. @ Week | | In Vivo @ Week | |
| Braid Number | Diameter, mm | Maximum Load Kpsi, (N) | Dose, kGy | 6 | 12 | 6 | 12 |
| 7-a | 0.38 | 80 (62) | 0 | 77 | 68 | 72 | 54a |
| | | | 5 | 68 | 57 | 60 | 50 |
| | | | 25 | 63 | 59 | 49 | 44 | a37% at 26 weeks.

TABLE III

Dose-modulated BSR Data for Braided Suture of Example 2

| | Initial Physical Properties | | | % BSR | | | |
|---|---|---|---|---|---|---|---|
| | | | | In Vitro @ 37° C. @ Week | | In Vivo @ Week | |
| Braid Number | Diameter, mm | Maximum Load Kpsi, (N) | Dose, kGy | 6 | 12 | 6 | 12 |
| 2 | 0.58 | 48 (84) | 0 | 78 | 71 | 72 | 67 |
| | | | 5 | 72 | 72 | 72 | 59 |
| | | | 25 | 67 | 49 | 60 | 52 |

TABLE IV

Dose-modulated BSR Data of Braided Suture of Example 3

| | Initial Physical Properties | | | % BSR | | | |
|---|---|---|---|---|---|---|---|
| | | | | In Vitro @ 37° C. @ Week | | In Vivo @ Week | |
| Braid Number | Diameter, mm | Maximum Load Kpsi, (N) | Dose, kGy | 6 | 12 | 6 | 12 |
| 3-f | 0.33 | 60 (35) | 0 | 95 | 93 | 93 | 85 |
| | | | 5 | 74 | 71 | 90 | 89 |
| | | | 25 | 88 | 79 | 75 | 71 |

Radiation and Radiochemically Sterilized Absorbable Monofilament Sutures with Dose Modulated Breaking Strength Retention (BSR) Profile Two types of monofilament sutures, designated as Examples 4 and 5, were produced by melt-spinning followed by an orientation using two polyaxial copolyester compositions as described in U.S. Pat. No. 6,462,169 (2002). The polymer of both sutures comprised a soft, amorphous, triaxial core made primarily of caprolactone and trimethylene carbonate and hard terminal crystalline block derived from more than 80 percent glycolide. The overall compositions of the polymers employed in forming the sutures of Examples 4 and 5 were 15/20/65 and 15/25/60 caprolactone/trimethylene carbonate/glycolide, respectively. The strength profile of radiation and radiochemically sterilized monofilaments are summarized below:

TABLE V

Dose-modulated BSR Data of Monofilament Sutures

| Suture of Ex. No. | Radiation Dose, kGy | Diameter, mm | Linear Strength, N | % In Vivo BSR at Week 1 | 2 | 3 |
|---|---|---|---|---|---|---|
| 4 | 0 | 0.27 | 36 | 75 | 52 | 26 |
|   | 5[a] |   |   | 70 | 42 | 22 |
|   | 25 |   |   | 58 | 29 | NT[b] |
| 5 | 0 | 0.30 | 35 | 77 | 52 | 22 |
|   | 5a |   |   | 65 | 35 | 18 |
|   | 25 |   |   | 54 | 27 | NT |

[a]Using the radiochemical process.
[b]NT = Too weak to test.

Radiation and Radiochemically Sterilized Absorbable Long-Lasting Braided Sutures with Dose Modulated BSR and Absorption Profile Two braided sutures having the same compositions as those of Examples 1 and 2, described in Table I, above, were prepared and denoted as A and B. The two sutures were of identical size and construction and were evaluated for their accelerated in vitro BSR and mass loss in a phosphate buffer at pH 12 and 50° C. The effects of radiation sterilization and radiochemical sterilization as to modulating the suture properties are summarized in Tables VI and VII. The data in those tables show that both the BSR and mass loss can indeed be modulated by controlling the radiation dose.

TABLE VI

Accelerated In Vitro Mass Loss Data of Size 2-0 Non-sterile (NS), Radiochemically Sterilized (RCS), and Radiation Sterilized (GS) Braids A and B

| Mass Data, % Loss @ | Braid | | | | | |
|---|---|---|---|---|---|---|
|   | A | | | B | | |
|   | Sterilization | | | | | |
| Day | NS | RCS | GS | NS | RCS | GS |
| 3 | 36.4 | 36.9 | 41.0 | 46.3 | 46.9 | 48.6 |
| 6 | 70.3 | 70.5 | 75.5 | 87.7 | 78.5 | 82.2 |
| 8 | 86.5 | 86.1 | 90.8 | 90.7 | 91.1 | 93.2 |

TABLE VII

Accelerated Breaking Strength Retention (BSR) Data of Non-sterile (NS) and Gamma-sterilized (GS) Braids A and B

| | | Braid | | |
|---|---|---|---|---|
| | | A | | B |
| | | Sterilization | | |
| | | NS | GS | NS | GS |
| Initial Max. Load[a], N | | 56.1 | | 48.4 | |
| Diameter, mm | | 0.36 | | 0.36 | |
| BSR[b], %, @ | 14 hours | 65 | 65 | 64 | 50 |
|              | 22 hours | 63 | 61 | 53 | 45 |

[a]Of non-sterile suture.
[b]Based on initial maximum load of non-sterile suture.

Example 6

Radiochemically Sterilized Tissue Adhesive Formulation

A methoxypropyl cyanoacrylate formulation containing less than 10 percent of a polyaxial copolyester of trimethylene carbonate, caprolactone, and glycolide [described as a polyaxial polymeric initiator in U.S. Pat. No. 6,462,169 (2002)] was prepared and packaged in a polyethylene, sealed ampoule under dry nitrogen. Several ampoules were placed in a hermetically sealed package containing 200 mg of Celcon-M90 polyformaldehyde. The entire package was irradiated with 5.2 kGy of gamma radiation. Using the fabric peel test described earlier [Flagle et al., Trans Soc. Biomater., 22, 376 (1999)], the peel strength of the irradiated and non-irradiated specimens were shown to be 22.05 and 36.25 N, respectively. The formulation viscosity remained essentially unchanged after irradiation.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A sterilized tissue adhesive having controllable adhesive joint strength when applied to living tissues, made by the process comprising the steps of:
   packaging a methoxyalkyl cyanoacrylate-containing formulation; and
   irradiating the packaged formulation with high energy radiation in the presence of a radiolytically generated formaldehyde at a dose in the range of from about 4 kGy to about 7 kGy;
   wherein the adhesive joint strength varies inversely with the radiation dose.

2. The tissue adhesive set forth in claim 1 wherein the high energy radiation comprises gamma-rays.

3. The tissue adhesive set forth in claim 1 wherein the high energy radiation comprises electron beam.

4. An absorbable ester-based medical device having a shortened breaking strength retention profile made by the process comprising the steps of:
   providing an absorbable, ester-based polymer comprising a high glycolide-based polymer comprising a segmented/block copolymer comprising at least 50 percent by weight of glycolide-based sequences the copolymer comprising a hard segment or block comprising greater than about 80 percent by weight glycolide and less than about 20 percent by weight of a monomer selected from the group consisting of l-lactide and trimethylene carbonate, and a soft segment or block comprising at least one cyclic monomer selected from the group consisting of caprolactone, trimethylene carbonate, lactide, p-dioxanone and 1,5-dioxepan-2-one;
   forming the polymer into a desired medical device configuration; and
   irradiating the formed device with high energy radiation at a dose in the range of from about 4 to about 7 kGy in the presence of a radiolytically generated formaldehyde;

wherein the breaking strength retention profile shortens with increasing radiation dosage.

5. An absorbable sterilized medical device as set forth in claim 4 wherein the step of forming the polymer into a desired medical device configuration comprises forming the polymer into a suture.

6. An absorbable sterilized medical device as in claim 4 wherein the absorbable, ester-based polymer comprises a segmented or block copolymer having a polyaxial chain geometry wherein the soft segments or blocks comprise an amorphous core and wherein the hard segments or blocks comprise crystalline terminal segments or blocks.

7. An absorbable sterilized medical device as set forth in claim 6 wherein the step of forming the polymer into a desired medical device configuration comprises forming the polymer into a suture.

* * * * *